(12) United States Patent
Murray et al.

(10) Patent No.: US 12,013,335 B2
(45) Date of Patent: *Jun. 18, 2024

(54) PORTABLE FLOW CELL DETECTOR COMPRISING A UV-LED EMITTING AT 235 NM

(71) Applicant: AQUAMONITRIX LIMITED, Tullow (IE)

(72) Inventors: Eoin Murray, Tullow (IE); Patrick Roche, Tullow (IE); Kevin Harrington, Tullow (IE); Matthieu Briet, Tullow (IE)

(73) Assignee: AQUAMONITRIX LIMITED, Tullow (IE)

( * ) Notice: Subject to any disclaimer, the term of this patent is extended or adjusted under 35 U.S.C. 154(b) by 0 days.

This patent is subject to a terminal disclaimer.

(21) Appl. No.: 17/582,252

(22) Filed: Jan. 24, 2022

(65) Prior Publication Data

US 2022/0214271 A1    Jul. 7, 2022

Related U.S. Application Data

(63) Continuation of application No. 17/057,224, filed as application No. PCT/EP2019/055206 on Mar. 1, 2019, now Pat. No. 11,237,099.

(30) Foreign Application Priority Data

Jun. 1, 2018   (IE) .................................. S2018/0161
Oct. 12, 2018  (IE) .................................. S2018/0322

(51) Int. Cl.
   *G01N 21/33*   (2006.01)
   *G01N 33/18*   (2006.01)

(52) U.S. Cl.
   CPC ............ *G01N 21/33* (2013.01); *G01N 33/188* (2013.01); *G01N 2201/0221* (2013.01); *G01N 2201/061* (2013.01)

(58) Field of Classification Search
   CPC ................. G01N 21/33; G01N 33/188; G01N 2201/0221; G01N 2201/061; G01N 21/05; H01L 25/167; H01L 33/483
   (Continued)

(56) References Cited

U.S. PATENT DOCUMENTS 9,752,978 B2     9/2017   Kraiczek et al.
2010/0136699 A1  6/2010   Drese et al.
2011/0309813 A1* 12/2011  Meier .................... G08C 19/02
                                              323/299

FOREIGN PATENT DOCUMENTS

JP   2009302576 A   12/2009
WO   2012137750 A1  10/2012

OTHER PUBLICATIONS

Li, Yan, et al. "Performance of a new 235 nm UV-LED-based on-capillary photometric detector." Analytical chemistry 88.24 (2016): 12116-12121.

(Continued)

*Primary Examiner* — Md M Rahman
(74) *Attorney, Agent, or Firm* — George Likourezos; Carter, DeLuca & Farrell LLP

(57) ABSTRACT

The present invention discloses an optical detection cell for detecting inorganic analytes in an aquatic environment. The optical detection cell comprises a microfluidic channel defining an optical detection path. First and second transparent windows are bonded at opposite locations on the microfluidic channel. The optical detection cell is provided with a UV-LED, and light detector respectively positioned proximally to the first and second transparent windows. The (Continued)

UV-LED configured to be driven by a constant electrical current having a value between 2.5 mA and 50.0 mA.

21 Claims, 13 Drawing Sheets

(58) Field of Classification Search
USPC .......................................................... 356/51
See application file for complete search history.

(56) References Cited

OTHER PUBLICATIONS

Moe, Craig G., et al. "AlGaN Light-Emitting Diodes on AlN Substrates Emitting at 230 nm." physica status solidi (a) 215.10 (2018): 1700660.

Schmid, Stefan et al. "UV-absorbance detector for HPLC based on a light-emitting diode." Analyst 133.4 (2008): 465-469.

Bui, Duy Anh et al. "A deep-UV light-emitting diode-based absorption detector for benzene, toluene, ethylbenzene, and the xylene compounds." Sensors and Actuators B: Chemical 235 (2016): 622-626.

Da Silveira Petruci, Joao Flavia, et al. "Absorbance detector for high performance liquid chromatography based on a deep-UV light-emitting diode at 235 nm." Journal of Chromatography A 1512 (2017): 143-146.

Li, Yan, et al. "High power deep UV-LEDs for analytical optical instrumentation." Sensors and Actuators B: Chemical 255 (2018): 1238-1243.

Macka, Mirek et al. "Light-emitting diodes for analytical chemistry." Annual Review of Analytical Chemistry 7 (2014): 183-207.

Beaton, Alexander D., et al. "Lab-on-chip measurement of nitrate and nitrite for in situ analysis of natural waters." Environmental science & technology 46.17 (2012): 9548-9556.

* cited by examiner

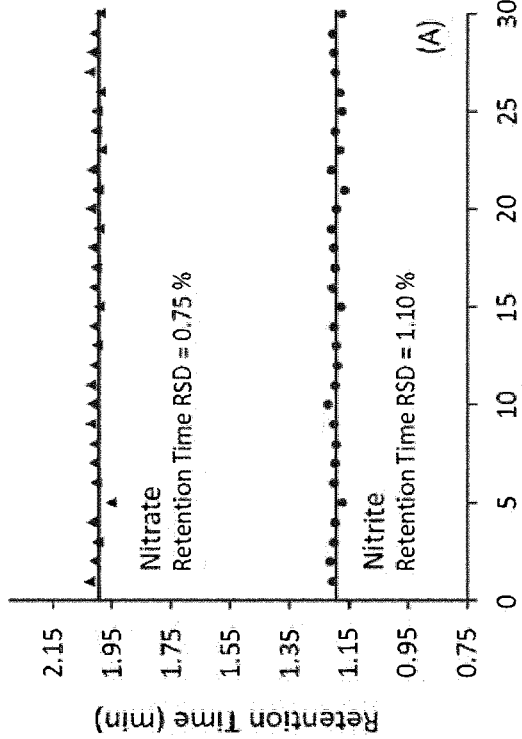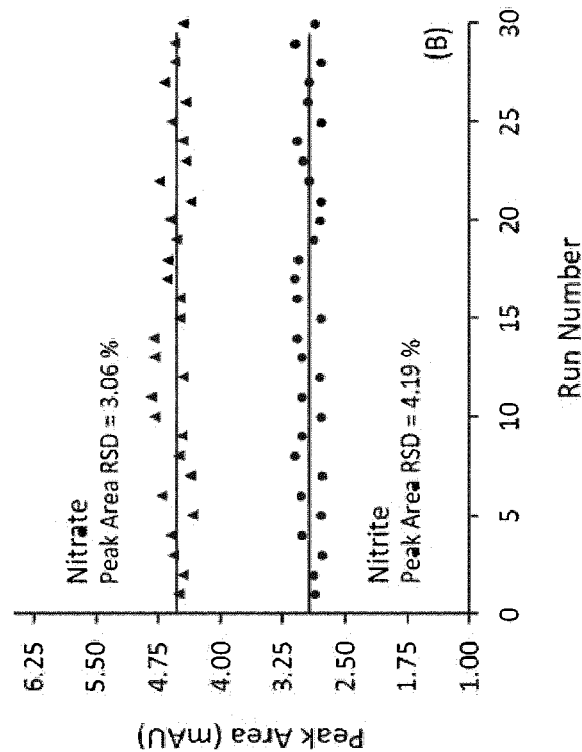
Figure 13A
Figure 13B

PORTABLE FLOW CELL DETECTOR COMPRISING A UV-LED EMITTING AT 235 NM

CROSS REFERENCE TO RELATED APPLICATIONS

The present application is a Continuation of U.S. patent application Ser. No. 17/057,224, filed Nov. 20, 2020, which claims the benefit of, and priority to, national stage entry of International Application No.: PCT/EP2019/055206, filed on Mar. 1, 2019 and claims priority to Application No. S2018/0322, filed in Ireland on Oct. 12, 2018 and Application No. S2018/0161, filed in Ireland on Jun. 1, 2018. The entire contents of the foregoing applications are hereby incorporated by reference.

FIELD

The present invention relates to an optical detection cell and a system for detecting inorganic analytes, such as nitrate, and nitrite in an aquatic environment, which may be used for monitoring water quality. More specifically, the present invention relates to an Ultraviolet (UV) based optical detection cell and a portable in-situ optical system for detecting inorganic analytes in an aquatic environment such as rivers, lakes, water reservoirs, and the like.

BACKGROUND

Over the past decade, anthropogenic activities such as agriculture, food production and industrial development have increased as a consequence of a growing global population. This increase in anthropogenic activity has significantly impacted freshwater quality. Excessive levels of nitrite and nitrate in freshwater present a notable risk to both environmental and human health. Accordingly, a range of legislative documentation has been set out both in Europe and globally in which the monitoring of nitrite and nitrate in freshwater bodies is a necessity.

Nitrogen in the form of nitrite ($NO_2^-$) and nitrate ($NO_3^-$) is naturally found in environmental waters. These anions play an integral role in facilitating the growth of algae and flora essential for aquatic ecosystems. Despite their intrinsic nature within environmental waters, excessive levels of nitrate and nitrite, as a consequence of point and nonpoint pollution sources derived from anthropogenic activities, present a notable risk to both environmental and human health. Both nitrite and nitrate contribute to eutrophication which results in the overproduction of algae and aquatic plants. Algal blooms readily produce toxins and bacteria which are harmful to human health. These blooms can also severely reduce oxygen levels in water which has a detrimental impact on aquatic life. In addition to environmental impacts, nutrient pollution also has a significant economic impact.

Currently, nitrite and nitrate monitoring in water predominantly take place on a manual basis. Water samples are collected and transported to centralised facilities for analysis, in a processed referred to as grab sampling. Grab sampling in combination with the standard chemical analysis is expensive, time-consuming and yields poor spatial and temporal data. To overcome these problems, low-cost in-situ technologies that provide continuous or semi-continuous observations are needed. Standard bench-top analytical instruments are not well suited to in-situ analysis due to their physical weight and size, power consumption and cost. As a consequence, it is not practical or cost-effective to attempt to use bench-top systems for in-situ water monitoring. In order to achieve truly effective water quality management, deployable, in-situ sensor systems capable of achieving high frequency and spatial data are required.

An example of a leading in-situ analyser for nitrate and nitrite, which employs colourimetric chemistries coupled with visible LED-based optical detection, is reported by A. D. Beaton, et al. in "Lab-on-Chip Measurement of Nitrate and Nitrite for In Situ Analysis of Natural Waters", Environ. Sci. Technol. 46 (2012) 9548-9556. However, these visible LED-based in-situ analysers require multiple reagents, and these reagents can be affected by temperature which may affect analytical accuracy over time. Furthermore, nitrate detection using colourimetry requires a reducing agent such as cadmium or vanadium chloride, which further increases complexity in operating, manufacturing, and maintaining the visible LED-based in-situ analyser.

As a less complex, more cost-effective approach to colourimetric based in-situ analysers, an in-situ analyser based on direct UV absorbance detection of nitrite and nitrate may be achieved using a low-cost deep UVC LED. As nitrite and nitrate have maximum wavelength values ($\lambda$max) of 209 and 200 nm respectively, a deep-UV LED of <240 nm enables direct absorbance-based detection of these analytes. The first demonstration of a 235 nm LED for chemical analysis, including direct detection of nitrite and nitrate, was reported by Li et al. in "Performance of a new 235 nm UV LED-based on-capillary photometric detector", Anal. Chem. 88 (2016) 12116-12121.2016.This system used standard benchtop capillary ion chromatography and integrated the 235 nm LED into a modified on-capillary detector made from a commercial optical interface. Within this detector set up, the UV-LED required high currents (up to 100 mA) to generate sufficient light intensity for capillary scale detection. This high current led to increased LED temperatures, and as LED performance decreases with increasing temperature, a heat sink for heat dissipation was required for LED operation. Comparably, Silveira Petruci et al. in "Absorbance detector for high-performance liquid chromatography based on a deep-UV light-emitting diode at 235 nm", J. Chromatogr. A 1512 (2017) 143-146, reported the use of a 235 nm LED for direct UV absorbance detection of pharmaceutical compounds with standard benchtop HPLC and again heat dissipation of the LED, in the form of a heat sink, was required for analysis. When considering the use of a 235 nm LED within a portable in-situ analyser, the use of a heat sink would increase complexity and cost associated with the development of the optical detector cell. Furthermore, the performance of the heat sink in mitigating heat may be affected over time, which may impact the accuracy and performance of the in-situ analyser.

SUMMARY OF THE INVENTION

The present invention aims to provide an optical detection cell for detecting inorganic analytes which absorb light within the UV spectrum that overcomes the disadvantages of the prior art solutions.

The present invention further aims to provide a portable system for monitoring water quality by detecting the level of inorganic analytes in an aquatic environment that overcomes the disadvantages of prior art solutions.

According to a first aspect of the present invention, An optical detection cell for the detection of inorganic analytes in a fluid sample, the optical detection cell comprising:
a detection cell body comprising
a microfluidic channel having first and second ends, which is configured to provide a detection path for the fluid sample,
a first opening for delivering a fluid sample to the microfluidic channel and a second opening for extracting fluid from the microfluidic channel, and
first and second UV transparent windows attached respectively to opposing first and second locations of the microfluidic channel;
an Ultra-Violet (UV) Light Emitting Diode (LED) proximally positioned to the first transparent window and configured when powered to emit a light at a UV wavelength range, which light is at least partially directed to the optical detection path of the microfluidic channel for the exposure of the fluid sample in the microfluidic channel; and
a light detector proximally positioned to the second transparent window and configured, when powered, for detecting the amount of UV light passing through the exposed fluid sample, the light detector being configured for generating at least one electrical signal having a value corresponding to the light being detected,
characterised in that the UV-LED is configured to be driven by a constant electrical current having a value between 2.5 mA and 35.0 mA. According to embodiments of the present invention, the UV-LED electrical current may be between 2.5 mA and 25.0 mA, preferably between 2.5 mA and 15.0 mA, and more preferably between 2.5 mA and 12.5 mA.

It has been found that the optical cell of the present invention eliminates the need for heat sinks or heat dissipation modules, which are necessary components in the systems presented in the prior art. The elimination of heat sinks or heat dissipation modules is achieved by operating the UV-LED with an electrical current having a value in the range specified above, i.e. between 2.5 mA to 35.0 mA, preferably between 2.5 mA and 15.0 mA, and more preferably between 2.5 mA and 12.5 mA. The electrical current may be generated by a power supply, such as a battery. It may be even more preferable that the higher range of the current value is maintained at or below 12 mA. By operating the UV-LED with a low-level electrical current, the heating problems encountered with the solutions of the prior art may be overcome. The optical detection cell may be combined with pumps for sample and fluid delivery and can be used to measure nitrate ($NO_3^-$) and nitrite ($NO_2^-$) through direct UV absorbance detection of the sample directly or following chromatographic separation of the sample, as $NO_3^-$ and $NO_2^-$ absorb within the UV range. It should be noted that the UV-LED may be operated at a higher current of over 35 mA, but the use of a heat sink may be necessary to dissipate the heat generated.

According to embodiments of the present invention, the diameter of the microfluidic channel is between 200.0 to 600 µm, preferably between 400.0 to 500.0 µm. According to embodiments of the present invention, the optical detection path has a length between 1.0 cm to 2.5 cm, preferably between 2.0 cm to 2.5 cm, and even more preferably between 2.0 cm to 2.15 cm.

Typical deep UV-LEDs have relatively low optical power output and commonly require high operating currents which results in the UV-LEDs generating heat. The LED lifetime, the emission wavelength, and the intensity of the LED at high current densities is negatively affected with increasing temperature. Therefore, heat sinks are typically required to dissipate heat generated by the LED, as shown in the systems of the prior art solutions. To increase the amount of light emitted from the UV-LED that can travel through the detection channel a microfluidic channel having a sufficiently wide aperture may be provided. For example, the diameter of the microfluidic channel may be between 200.0 to 1000 µm, and even more preferably between 400.0 to 500.0 µm. At the same time, the length of the optical detection path may be between 1.0 cm to 2.5 cm, preferably between 2.0 cm to 2.5 cm, and even more preferably between 2.0 cm to 2.15 cm. Due to at least the sufficient wide aperture, sufficient amount of light from the UV-LED may travel through the optical detection path, thus allowing a low-intensity light emitted for a UV-LED operated at low current, e.g. below 10 mA, to be used for the detection of inorganic analytes. As a result, with the use of a microfluidic channel of at least a sufficiently wide aperture, in the ranges defined above or greater, may reduce the electrical current needed to be applied to the UV-LED, and thus reduce the heating of the LED. Preferably, to reduce the heat dissipated by the LED while maintaining accuracy, the UV-LED used in the present invention may be operated at low currents <12 mA. It should be noted that according to the present invention, the UV-LED is operated at a current range which is well below the operating current reported in the prior art solutions. It should be noted that other methods known to the skilled person in the art for lowering or efficiently removing the heat dissipated by the UV-LEDs may also be used in the present invention. These known techniques may involve the use of a heat sink, lowering the LED current, or any other known method.

According to embodiments of the present invention, the UV-LED is configured to emit UV light at a range between 100.0 to 400.0 nm, preferably at a range between 200.0 to 300 nm, and more preferably at a range between 200.0 to 280.0 nm.

It has been found that with the use of a UV-LED emitting light it may be possible to directly detect inorganic analytes which absorb light within the UV wavelength of the light emitted from the UV-LED, e.g. nitrite, nitrate, iodide, iodate and others. For example, nitrite and nitrate have maximum absorption wavelength values ($\lambda$max) of 209 and 200 nm respectively, thus requiring a deep-UV LED of <240 nm, such as the one provided by the present invention, to enable direct absorbance-based detection of these analytes. The UV LED may be of the desired wavelength within the UV, or deep UV range, e.g. 235, 250, or 280 nm LED.

According to embodiments of the present invention, the transparent windows are UV transparent windows made from glass.

It has been found that the use of glass windows enables higher transmission of light, emitted from the UV-LED, through the optical detection path of the microfluidic channel. As a result of the higher transmission of light through the optical detection path, the accuracy of the optical detection cell may be improved. Furthermore, the higher transmission of light may enable the UV-LED to be operated with an electrical current having a value between 2.5 mA and 12 mA. The transparent windows may be made from a material such as fused silica glass or sapphire. For example, the transparent windows may be positioned on each end of the microfluidic channel. The UV transparent windows allow for UV absorption to be measured using a UV Light Emitting Diode (LED) proximally located to one of the transparent windows and a UV-sensitive photodiode proximally located to the opposing transparent window.

According to embodiments of the present invention, the light detector is a photodiode configured for detecting emitted light at the wavelength range of the UV-LED.

The photodiode is a semiconductor device that converts light into an electrical current. The current is generated when photons are absorbed in the photodiode. Photodiodes may contain optical filters, built-in lenses, and may have large or small surface areas. It has been found that by using a photodiode capable of detecting light at the wavelength range of the UV-LED, may improve the accuracy of the optical detection in detecting inorganic analytes.

According to an embodiment of the present invention, the microfluidic channel has a z-shape or any other shape whereby the light source and the light detector can be positioned opposite one another.

It has been found that a z-shape microfluidic channel allows the UV-LED and light detector to be positioned opposite one another thus enabling the detection of inorganic analytes in the fluid sample. It should be noted that the microfluidic channel may be provided in any other shape that allows for the UV-LED and light detector to be positioned opposite one another, such shapes may be formed in two-dimensional (2D) or three-dimensional (3D) space.

According to embodiments of the present invention, the optical detection cell body comprises a first and a second layer bonded to one another. The microfluidic channel may be formed on the first layer and/or the second layer.

The first and second layers may be fabricated through micro-milling and solvent vapour bonding of two layers of poly (methyl methacrylate) (PMMA), which are non-transparent to UV light allowing for maximum transmission of light through the optical detection path. It should be noted that other materials may be used instead that maximise light transmission of light through the optical detection path of the microfluidic channel, such as metal.

According to embodiments of the present invention, the first and second transparent windows are bonded on respective apertures created on the optical detection cell body. The respective apertures may be of equal size to the diameter of the microfluidic channel. The respective apertures may be formed as a recess at the desired location. The recess may have a predetermined depth to accommodate the thickness of the UV transparent windows. For example, the depth of the aperture may be equal to the thickness of the UV transparent windows, so that when the UV transparent windows are positioned in the respective aperture their top surface, facing the LED, and the Light detector is flush with the surface of the optical detection cell body. The transparent windows may be bonded using a suitable epoxy configured to provide a watertight seal so as to prevent leaks of the fluid sample from the microfluidic channel.

According to a second aspect of the present invention, a portable system for detecting inorganic analytes in a fluid sample may be provided. The system comprising:
  an optical detection cell according to the first aspect of the present invention;
  at least one pump module coupled to an opening of the optical detection cell body, the at least one pump module being configured for delivering a fluid sample to the optical detection path of the microfluidic channel for exposure to the UV-LED of the optical detection cell;
  a sample intake module configured to provide a fluid sample of a predetermined volume to the at least one pump; and
  a processing unit configured for processing the at least one signal generated by the light detector of the optical detection cell to compute the levels of inorganic analytes in the fluid sample; and
  a power source providing at least one electrical signal for powering at least one of the optical detection cell, and/or the at least one pump, and/or the sample intake system, and/or the processing unit.

It has been found that the portable system of the present invention has a number of advantages when compared with existing solutions. The portable optical detection system may be utilised for the direct UV absorbance detection of inorganic analytes, such as nitrite, nitrate, iodide, iodate and other inorganic analytes which absorb within the UV spectral region. The optical cell and system of the present invention, when combined with the electronics for LED control and data acquisition, is more portable, smaller in size and uses less power compared to other commercially available systems. For example, the size and power consumption of the system of the present invention is significantly smaller in comparison to the system known in the art. The reduction in size and power consumption is obtained by providing an optical detection cell, as previously described, that uses a UV-LED as a light source, which may be operated at a very low current, e.g. less than 12 mA, thus eliminating the need for the integration of a heat sink, which is an integral component of the systems in the prior art solutions.

Furthermore, the cost and time required for manufacturing the system of the present invention are significantly lower when compared to conventional solutions. This is because, the system of the present invention is simpler in its construction, and requires fewer parts than a conventional system. For example, the manufacturing process of the cells may be simplified using rapid prototyping techniques such as 3D printing and micro-milling.

According to embodiments of the present invention, the pump module comprises a pump configured for delivering eluent from an eluent source to a micro-injection valve, the micro-injection valve being configured for supplying the fluid sample and the eluent to a guard anion exchange column configured for separating the compounds in the fluid sample delivered to the microfluidic channel of the optical cell.

It has been found that with the present invention, the optical detector, combined with a deep UV-LED, may be coupled with an automated pump, sample intake system, microinjection valve and anion exchange column to generate a portable ion chromatography (IC) system for nitrite and nitrate analysis. This system is less complex compared to leading in-situ analysers for nitrate and nitrite which employ colourimetric chemistries coupled with LED-based optical detection. These colourimetry systems, as described in the background section, require numerous chemical reagents and complex fluidic control for analyte detection. While for nitrate analysis using colourimetry, a reduction step to nitrite is most typically required for detection.

According to embodiments of the present invention, the sample intake system comprises at least one syringe configured for injecting a fluid sample of a predetermined volume into the pump module.

The optical detection system may be coupled with automated pumps and sample intake system using syringes pumps integrated with, for example, stepper, brushed or brushless DC motors controlled by a microcontroller for eluent pumping and sample injection. A closed loop control system, for example, a system based on proportional-integral-derivative (P.I.D) control, may be used to control flow rate and injection volumes ensuring repeatable flow rates.

According to embodiments of the present invention, the processing unit is configured to control and operate one of the UV LED light source, the pumping module, and/or the sample intake system.

It has been found that an embedded system, such as a processing unit, comprising a microcontroller and constant current driver may be used to control and operate the UV LED light source while analogue signal generated by the photodiode can be sent to an analogue to digital converter. Data can then be stored locally, e.g. on a microSD card, for processing and analysis. The embedded system may be connected to a communication network to enable the portable system to be remotely accessed and operated. For example, the system may be connected to an Internet of Things network, which may allow for the communication of data collected from the portable system to a centralised facility, where the data may be processed and analysed. The data communicated may comprise data related to the inorganic analytes detected, and/or data related to the operation of the portable system modules, e.g. malfunction, shutdown, and the like. The communication of data to a centralised facility thus may also enable the continuous monitoring of the portable system functionality.

According to embodiments of the present invention, the optical cell is secured on a base, the base comprising a holder for the UV LED and a light detector holder.

It has been found that by providing the base and the UV-LED and light detector holders, it is possible to align the position of the LED and photodiode against the UV transparent window more accurately, thereby increasing the overall accuracy of the UV optical detection. The base may be configured for releasably securing the optical cell of the portable system. For example, the base may be provided with an opening dimensioned for releasably securing the optical cell. The LED holder and the light detector holder may be arranged for securing the position of the UV LED and photodiode against the opposing transparent windows on the base.

According to embodiments of the present invention, the base comprises means for guiding the UV-LED and light detector holders to the desired position with respect to the corresponding transparent windows. For example, the guiding means may be in the form of rails.

The guiding means may enable the LED and light detector holders to be movable along a predetermined direction on the base. The guiding means, e.g. the rails, may be positioned on opposite sides of the base. In this way, the system can accommodate optical cells of different dimensions, while maintaining substantially the same accuracy. Furthermore, with the use of guiding means lateral movement of the holders during operation may be prevented. As a result, the alignment between the UV-LED and light detector may be maintained during operation thus enhancing the accuracy of the optical detection cell in detecting inorganic analytes.

According to embodiments of the present invention, the guiding means comprise means for securing the UV-LED and light detector holders at the desired position.

It has been found that with the use of securing means, the desired position of the UV-LED holder and the light detector holder against the respective transparent windows may be further secured, thus increasing the accuracy of the portable system in detecting inorganic analytes.

BRIEF DESCRIPTION OF THE DRAWINGS

The following drawings are provided as an example to explain further and describe various aspects of the invention.

FIGS. 13a and 13b show the results of a repeatability study over 30 sequential runs.

DETAILED DESCRIPTION

The present invention will be illustrated using the exemplified embodiments shown in FIGS. 1 to 13 which will be described in more detail below. It should be noted that any references made to dimensions are only indicative and do not restrict the invention in any way. While this invention has been shown and described with reference to certain illustrated embodiments thereof, it will be understood by those skilled in the art that various changes in form and details may be made therein without departing from the scope of the invention encompassed by the appended claims. Furthermore, while the invention has been described with references to a particular optical detection cell and a portable system for detecting inorganic analytes, it should be understood by those skilled in the art that changes in the form and details may be made to facilitate other types of optical detection cells and systems for detecting inorganic analytes without departing from the scope of the invention encompassed by the appended claims.

Figure 1:
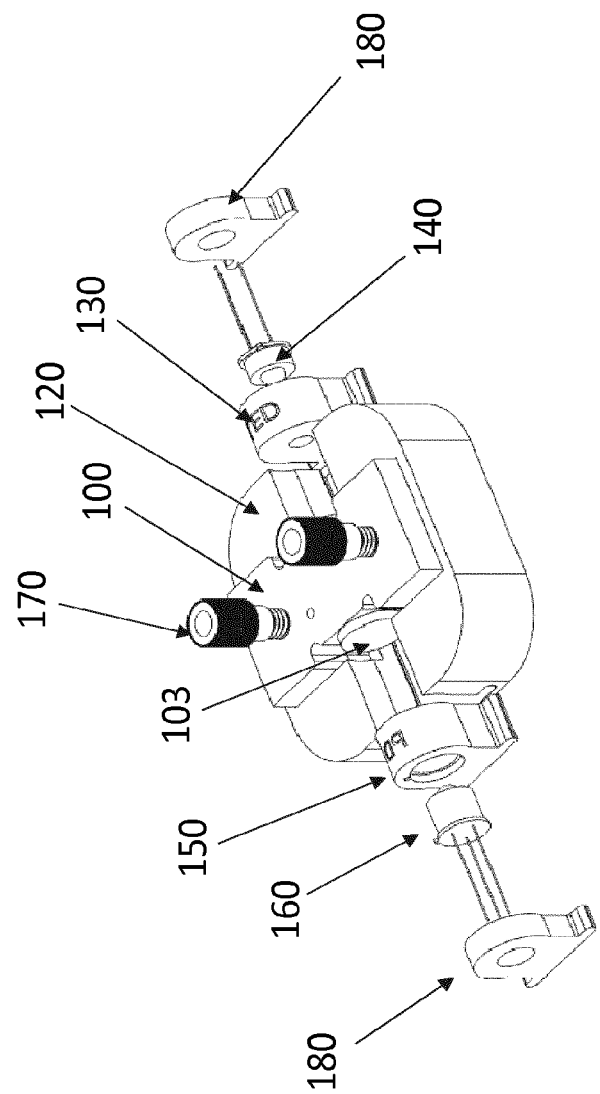
FIGS. 1 and 2 show an exemplified implementation of the optical detection cell according to embodiments of the present invention.
Figure 2:
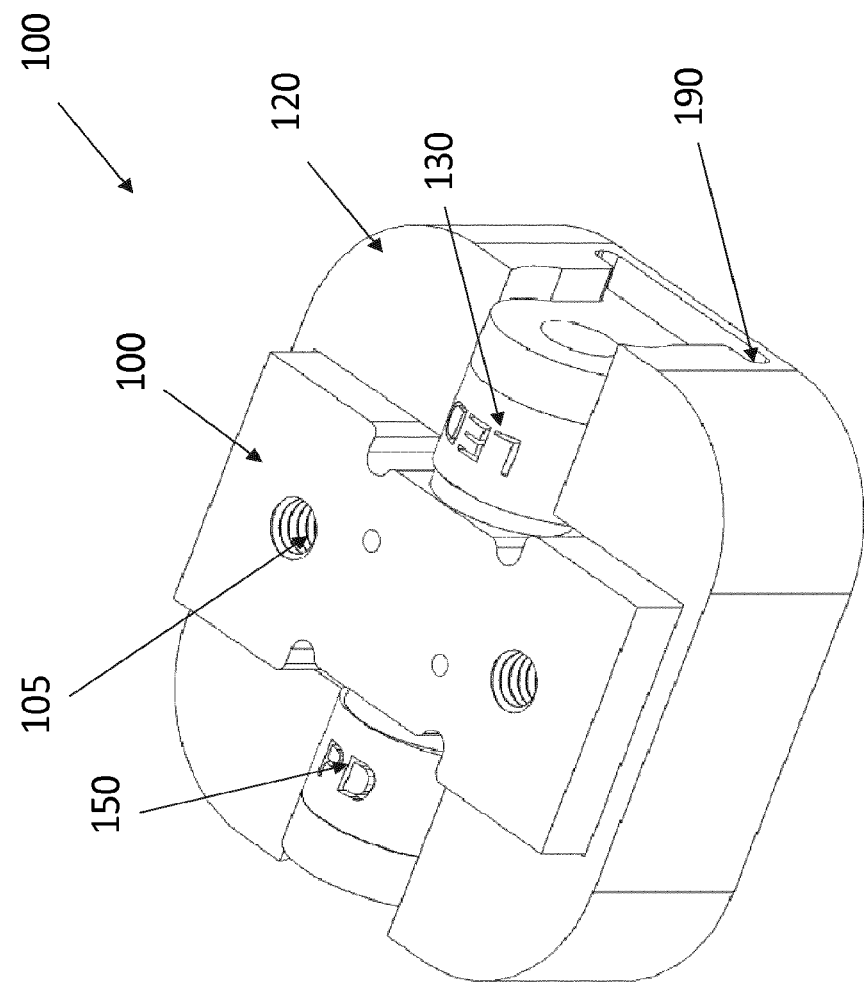
Figure 3:
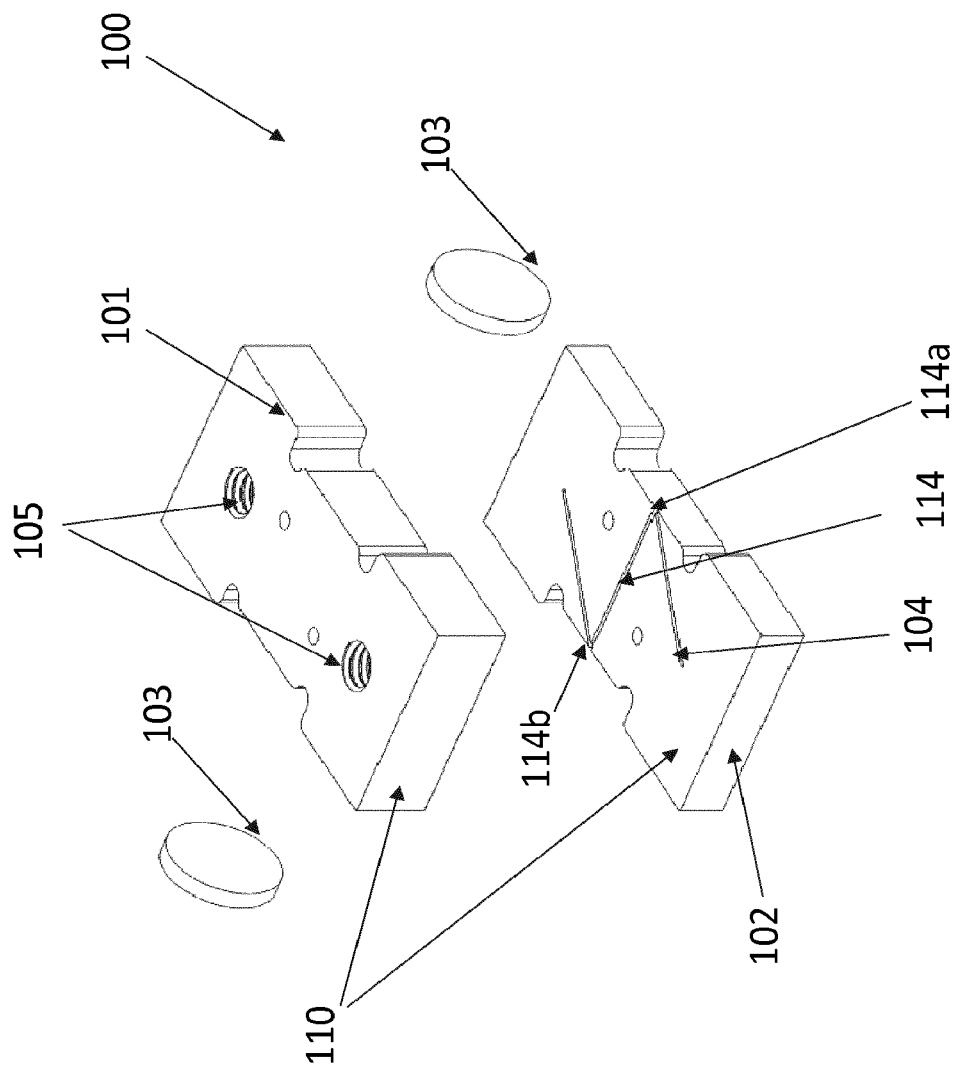
FIG. 3 shows an exemplified implementation of the optical detection cell body according to embodiments of the present invention.

FIGS. 1 to 3 show an example of a UV optical detection cell 100 for monitoring water quality by detecting inorganic analytes in an aquatic environment according to embodiments of the present invention. The optical detection cell 100 is provided with a detection cell body 110. As shown in FIG. 3, the detection cell body 110 may be provided with a top layer 101 and a bottom layer 102, which may be bonded to one another using an epoxy or another bonding agent. The detection cell body 110 may be provided with a microfluidic channel 104 having first and second ends, which is configured to provide an optical detection path 114 for exposing a fluid sample to the light emitted from a light source 140, e.g. an Ultra-Violet (UV) Light Emitting Diode (LED). The microfluidic channel 104 may be formed in the bottom layer 102 and/or the top layer 101. In the example shown in FIG. 3, the microfluidic channel 104 may be milled or etched on the bottom layer 102 having a desired shape, e.g. z-shape. The microfluidic channel 104 may be provided with a diameter between 200.0 to 600 μm, preferably between 400.0 to 500.0 μm. Furthermore, the optical detection path 114 defined in the microfluidic channel may have a length between 1.0 cm to 2.5 cm, preferably between 2.0 cm to 2.5 cm, and even more preferably between 2.0 cm to 2.15 cm. As shown in FIG. 3, the top layer 101 may be provided with openings 105 for pumping the analyte solution through the microfluidic channel 104. One of the openings 105 may act as an inlet, while the other may act as an outlet. As shown in FIG. 1, pumping connecting elements 170 may be secured in the respective openings 105, e.g. screwed or press-fitted, to allow for a pumping device to be connected to the detection cell body 110. Transparent windows 103 may be bonded at predetermined locations on the microfluidic channel 104 using epoxy or another bonding method known to the skilled person in the art. The transparent windows 103 may be positioned opposite one another. For example, the transparent windows 103 may be positioned at opposing locations 114a, 114b along the optical detection path 114 defined in the microfluidic channel 104, as shown in FIGS. 1 to 3. The transparent windows 103 may be made from a transparent material having desired light transmission properties, such as fused silica glass or sapphire. Returning to FIGS. 1 and 2, a UV Light Emitting Diode (LED) 140 may be proximally located to one of the transparent windows 103, and a UV-sensitive photodiode 160 may be proximally located at the opposing transparent window 103. According to embodiments of the present invention, the UV LED 140 may be of a predetermined UV wavelength, e.g. 235, 250, 280 nm LED. To reduce the heat dissipated by the UV-LED during operation, the UV-LED may be driven by an electrical current having a value between 2.5 mA and 35.0 mA, preferably between 2.5mA and 25.0 mA, more preferably between 2.5 mA and 15.0 mA, and even more preferably between 2.5 mA and 12.5 mA. Preferably the UV-LED may be operated with an electrical current having a value of 12.0 mA or below. The transparent windows 103 may be in the form of UV transparent windows 103 to ensure transmission of light, emitted from the UV-LED, through the optical detection path 114 of the microfluidic channel 104. As a result of the higher transmission of light through the optical detection path, the accuracy of the optical detection cell may be improved. Fibre optic cables may also be integrated at each end of the microfluidic channel to enable light transmission and absorbance detection.

Figure 4:
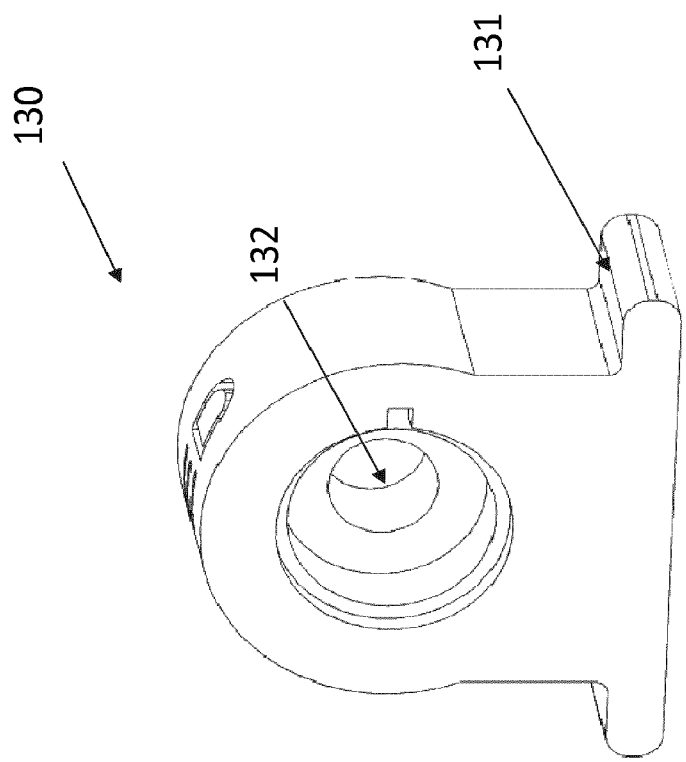
FIGS. 4 and 5 show exemplified implementations of the LED and photodiode holders according to embodiments of the present invention.
Figure 5:
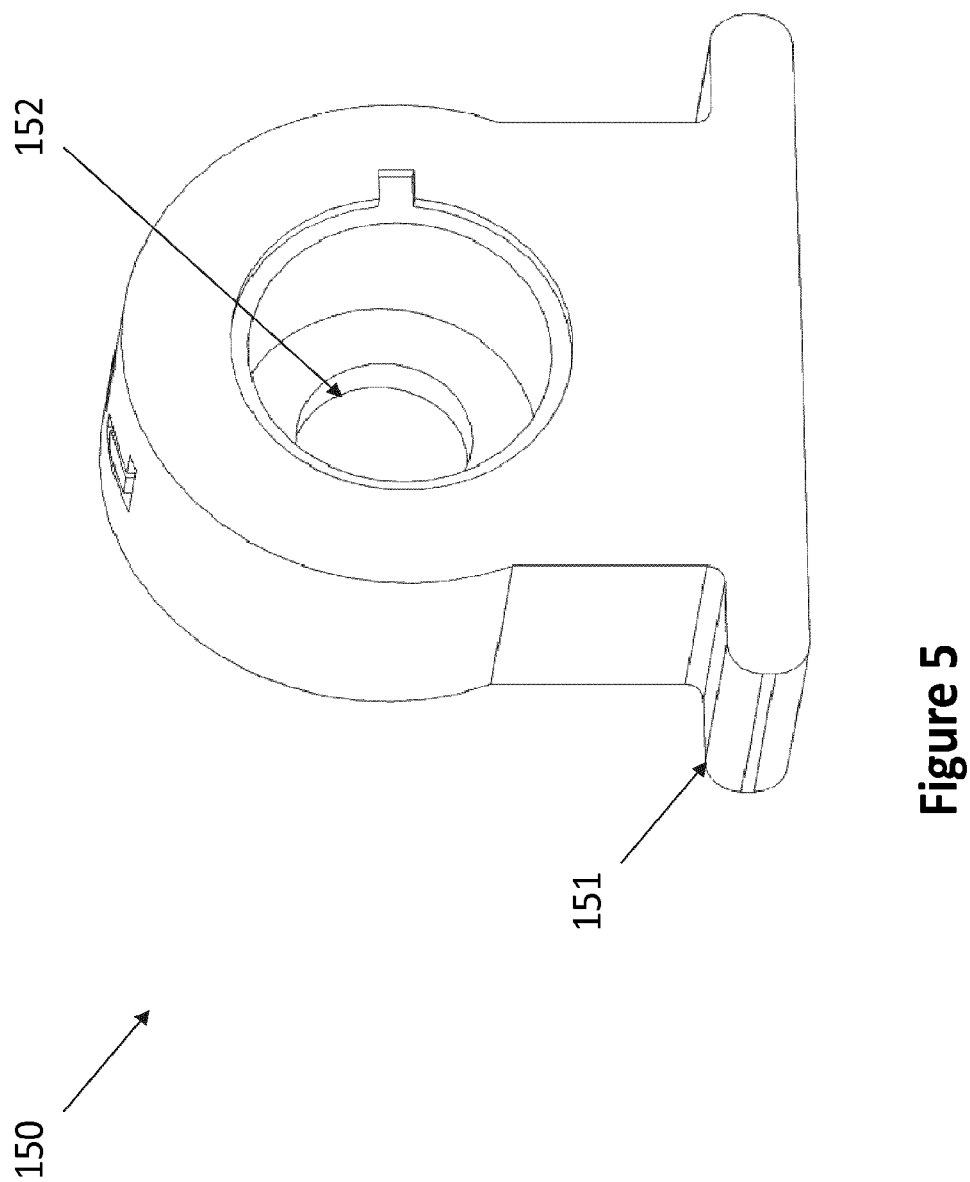

As shown in FIGS. 1 and 2, the optical detection cell 100 may be releasably secured on a base 120, which may be provided with an LED holder 130 and a photodiode holder 150, the holders being arranged for respectively securing the position of the UV LED 140 and UV photodiode 160 with respect to the transparent windows 103. The UV-LED holder 130 and the photodiode holder 150 may be movable on the base 120 along a predetermined direction so that they can be accurately positioned with respect to the transparent windows 140. The base 120 may be provided with guiding means 190, e.g. rails provided in the form of a recessed channel on the base 120, which can be used for guiding the UV-LED holder 130 and photodiode holder 150 to the desired location along a predetermined direction. As shown in FIGS. 4 and 5, the UV-LED holder 130 and the UV-photodiode holder 150 may be provided with openings 132 and 152, each respective arranged for receiving and securing a UV-LED 140 and a photodiode 160. The holders 130 and 150 may be provided with means 131, 151 for engaging with respective edges of the guiding means 190 of the base 120, which allow for the movement of the UV-LED 140 and UV-photodiode 160 along the base 120. To prevent further movement of the UV-LED and UV-photodiode holders 130, and 150 on the guiding means 190, securing elements 180 may be provided at each end, as shown in FIGS. 1 and 2.

Figure 6:
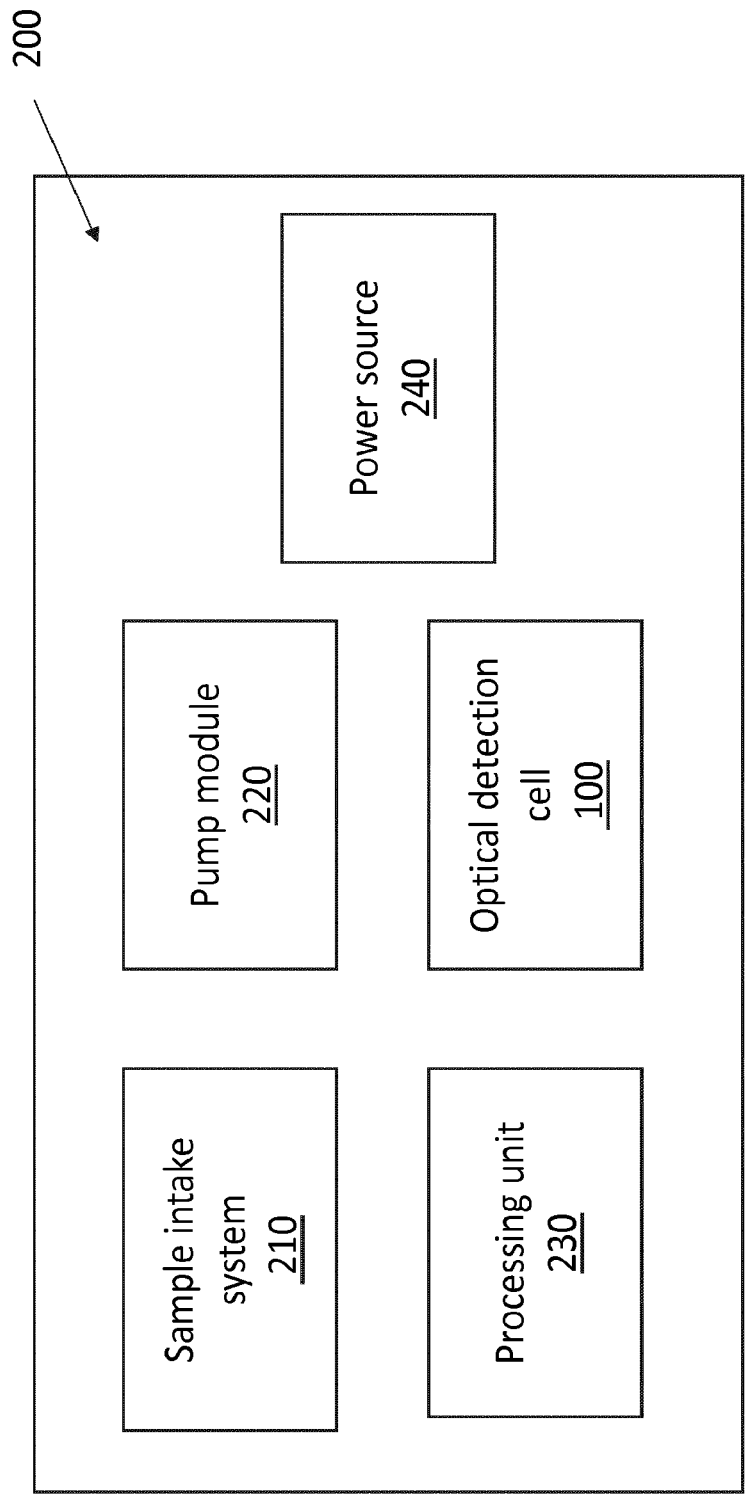
FIGS. 6 and 7 show an exemplified system for detecting inorganic analytes according to embodiments of the present invention.
Figure 7:
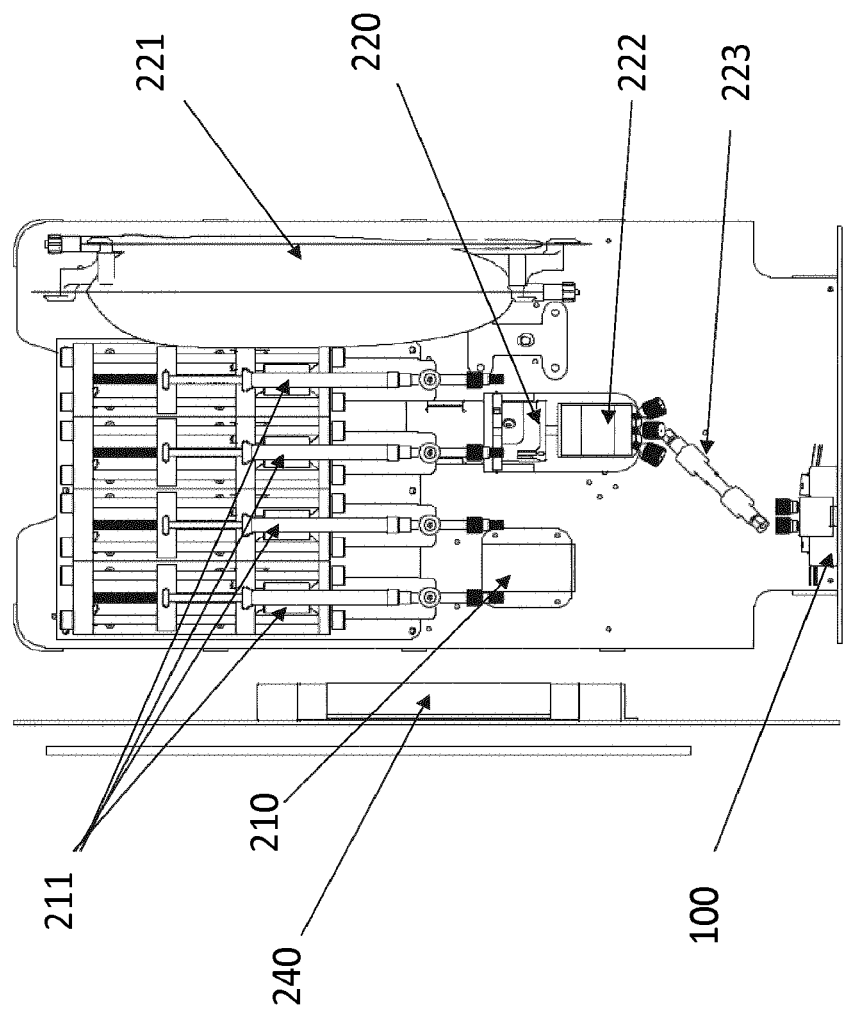

FIGS. 6 and 7 show an example of a portable system 200 for detecting inorganic analytes in an aquatic environment according to embodiments of the present invention. The portable system 200 may be used for the detection of nitrate and nitrite analysis in wastewater, or for other inorganic analytes that absorb light at the UV wavelength of the light emitted from the UV-LED. The system 200 may be provided with at least one pump module 220 coupled to an opening of the detection cell body 110 of the optical detection cell 100. The at least one pump module 210 is configured for delivering a fluid sample to the optical detection path 114 defined in the microfluidic channel 104, which is exposed to the light emitted from the UV-LED 140 of the optical detection cell 100. A sample intake module 210 may be provided for a fluid sample of a predetermined volume to the at least one pump from an aquatic environment, e.g. lake, wastewater plants, rivers, and the like. A processing unit 230 may be provided for processing the at least one signal generated by the light detector 160, e.g. the UV-photodiode of the optical detection cell 100 so as to compute the levels of inorganic analytes in the fluid sample. The system 200 may be provided with a power source 240, e.g. a battery, solar panel operated battery and the like. The power source 240 may be configured to provide at least one electrical signal for powering at least one of the optical detection cell, and/or the least one pump, and/or the sample intake system, and/or the processing unit. For example, the power source may be coupled with an electrical signal generator, which may be configured for generating an electrical signal having predetermined electrical characteristics, e.g. voltage and/or current levels, which may be adapted to requirements of each of the modules of the system 200. The system may be provided with automated low-pressure syringes 211 for pumping and fluid sample intake. This automation was achieved through the coupling of syringes 211, housed within 3D printed holders, with a microcontroller and brushed DC motors in order to pump eluent from an eluent source 221 and inject sample. A closed loop control system (e.g. P.I. or P.I.D. control) was used to precisely control the flow rate and injection volumes. For example, the pump module 220 may be provided with a pump configured for delivering eluent from an eluent source 221 to a micro-injection valve 222, the micro-injection valve 222 being configured for supplying the fluid sample and the eluent to a guard column 223 configured for separating the compounds in the fluid sample delivered to the optical detection cell 100, as shown in FIG. 7. The guard column 223 may be an anion exchange guard column (AG15) used for anion separation. The analogue signal generated by the UV photodiode 160 during analysis may be sent to a 16-bit analogue to digital converter, which may be part of the processing unit 230. Data generated for each sample may be arranged into a comma-separated value (CSV) format and stored on a microSD card in a CSV file for post-processing and generation of chromatograms. The processing unit 230 may be configured to control and operate one of the UV LED light source 140, the pumping module 220, and/or the sample intake module 210.

Figures 8A, 8B:
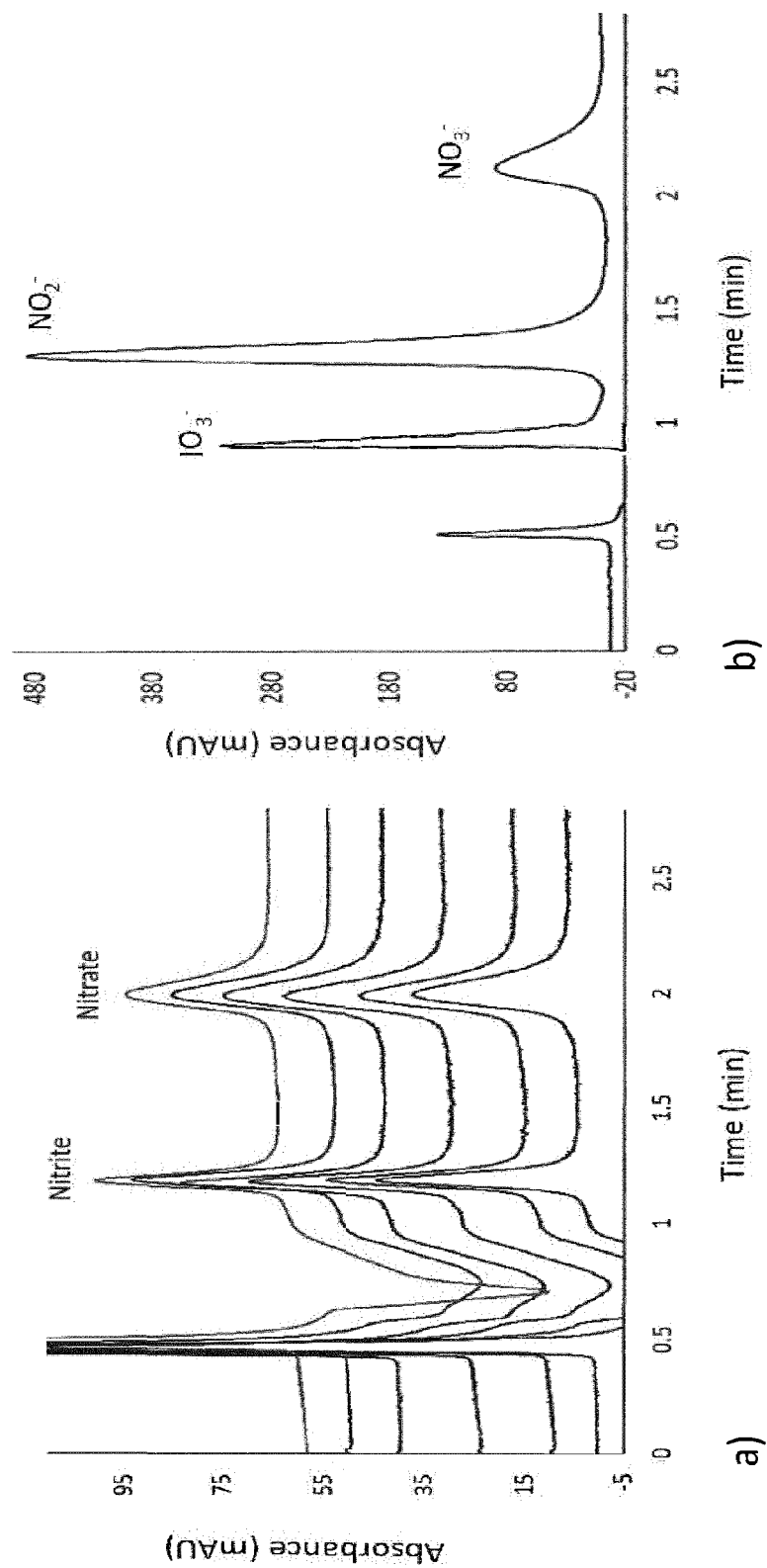
FIGS. 8a and 8b show empirical results demonstrating the repeatability and the selective detection capabilities of the optical detection cell according to embodiments of the present invention.

FIGS. 8a and 8b show empirical results obtained from a set-up using an optical system according to embodiments of the present invention. Using a High-Performance Liquid Chromatography (HPLC) pump, under isocratic conditions with a sample injection volume of 150 μL and using an anion exchange guard column, both analytes are detected in under 2.5 minutes. Analyte detection is achieved using the optical detector coupled with a 235 nm LED operated at a current of 9.5 mA. A back pressure of 10 bar is generated by the system, allowing for a portable eluent pump to be used with the system. The detector system employs custom-built electronics, as previously described, to control and monitor the operation of the different modules of the system thus facilitating portability and a reduction in system cost. Using the described system set up linear ranges of 0.015-35 and 0.050-70 mg/L were obtained, for $NO_2^-$ and $NO_3^-$ respectively, with a limit of detection (LOD) of 0.007 mg/L for $NO_2^-$ and 0.045 mg/L for $NO_3^-$. By altering the injection volume, linear range and limit of detection (LOD) values may be modified allowing for the detector to be used for the analysis of a wide range of sample matrices. Overlaid chromatograms of nitrite (1 mg/L) and nitrate (3 mg/L) generated by the system are displayed in FIG. 8a, highlighting detector repeatability. The selectivity achieved by the present approach is demonstrated in FIG. 8b as both nitrite and nitrate are suitably resolved in the presence of eight other typical small inorganic anions. FIG. 8a shows the repeatability of six sequential chromatograms measured using an optical detection cell 100 according to embodiments of the present invention, with six chromatograms overlaid. Each chromatogram represents isocratic separation of nitrite (1 mg/L $NO_2^-$) and nitrate (3 mg/L $NO_3^-$) using a Dionex Ultimate 3000 pump, microinjection valve, AS15 guard column, an optical detection cell with a 235 nm UV-LED operated with an electrical current of 9.5 mA, which is coupled to electronics for processing the results obtained. Set-up condiction conditions for the results shown in FIG. 8a: 100 mM KOH eluent at 0.8 mL/min, the sample volume was 150 µL. Set-up condiction conditions for the results shown in FIG. 8b: Isocratic separation of anion mix standard (10 mg/L $F^-$, $Cl^-$, $Br$, $NO_2^-$, $NO_3^-$, $IO_3^-$, $I^-$, $CO_3^{2-}$, $PO_4^{3-}$ and $SO_4^{2-}$) using Ion Chromatography (IC) set up.

Figure 9:
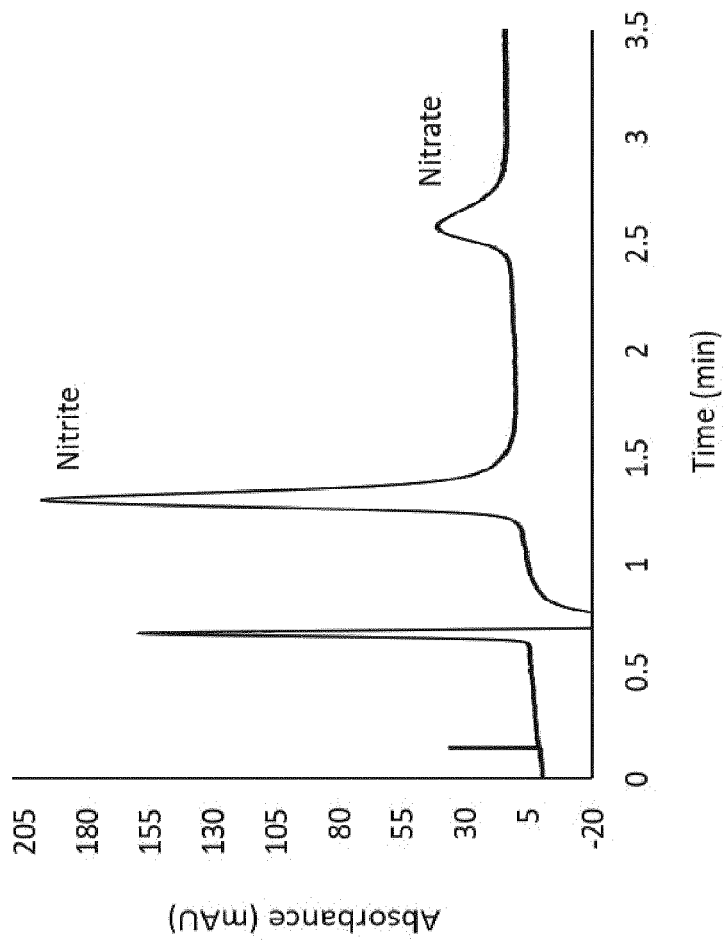
FIGS. 9 and 10 shows a chromatogram generated by an optical detection cell with a UV-LED operated respectively at 7 mA and 2.5 mA.

FIG. 9 shows empirical results obtained using a portable IC system with an optical detection cell 100 according to embodiments of the present invention for the in-situ analysis of septic system wastewater. An eluent of 130 mM KOH at 0.7 mL/min and a sample volume of 9 µL were used with a 235 nm LED operated at 7.0 mA in the described optical detection cell 100, also referred to as a detector. The concentration of $NO_2^-$ and $NO3^-$ within the wastewater was 35 mg/L and 50 mg/L respectively.

Figure 10:
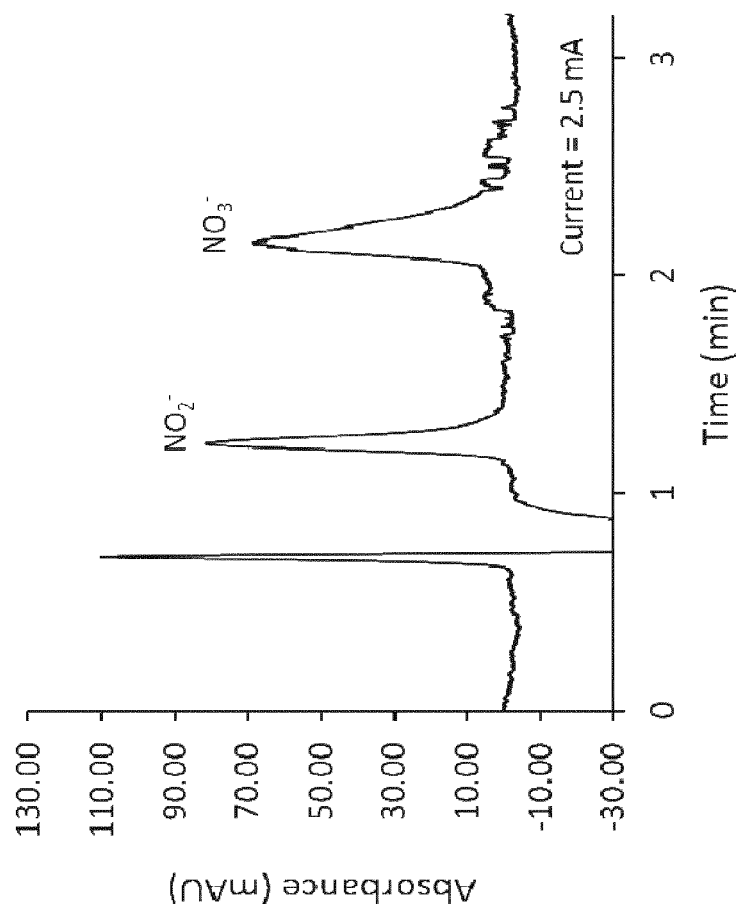

FIG. 10 shows empirical results obtained using a portable IC system with an optical detection cell 100 according to embodiments of the present invention for the in-situ analysis of wastewater. An eluent of 130 mM KOH at 0.7 mL/min, a sample volume of 10 µL with 235 nm LED operated at the low current of 2.5 mA. Baseline noise is more significant at this very low current; however, analyte detection is still achieved.

Thermal Study of LED and Detector

Figure 11:
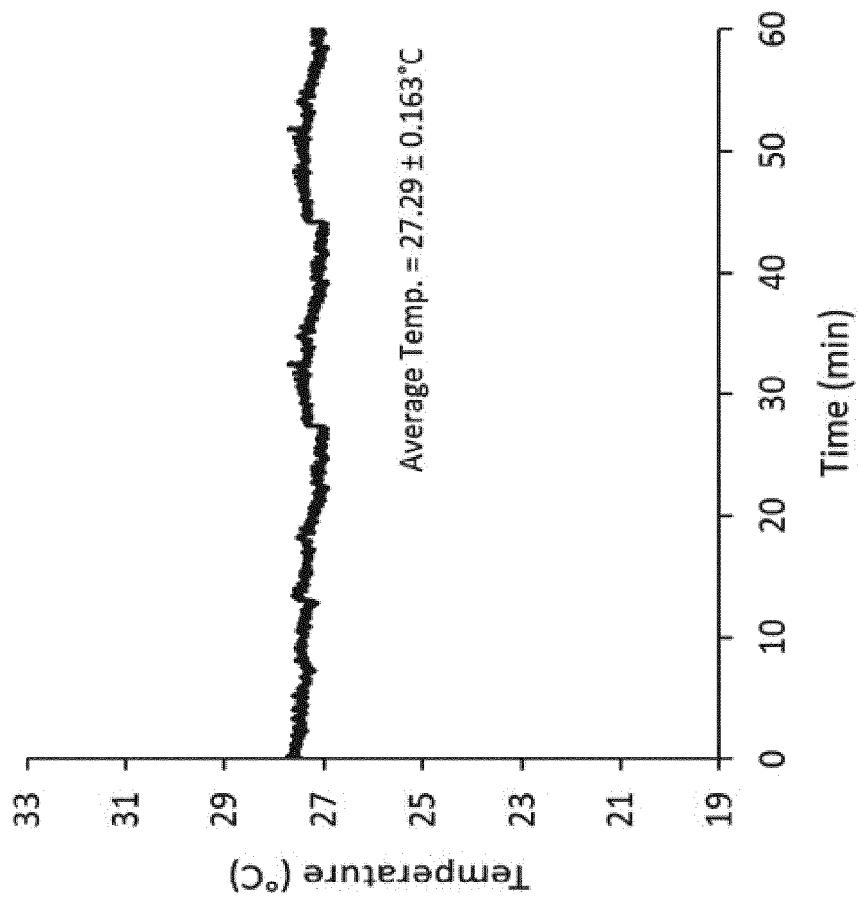
FIG. 11 shows temperature measurements of a 235 nm LED operated at low currents over one hour of continuous operation.

It has been established that thermal management of deep-UV LEDs 140 is an important consideration when employed for analytical operations. High currents are most typically applied for analysis using the UV-LEDs 140 and electrical power not converted into light is converted into heat. With increasing UV-LED temperature, luminous efficiency decreases, emission wavelengths shift and UV-LED 140 lifetime is reduced. In recent works in which the 235 nm LED 140 was used for optical detection with chromatographic analysis, the use of a heat sink for heat dissipation was essential to achieve analytical performance as currents of 100 mA, and 66 mA was used to operate the UV-LED 140, as discussed in the background section. Due to at least the diameter of the microfluidic channel 104 of the present invention, e.g. 500 µm channel dimensions, within the current optical detection cell 100 and alignment of the UV-LED 140 and photodiode 160 which was achieved by the 3D printed holders and housing, it was found that effective analyte detection could be achieved operating the LED 140 within the detector at a constant current of below 12 mA, e.g. between 2.5 mA to 12 mA. Under these conditions, a baseline noise signal was evaluated over 60 seconds, and the maximum deviation was recorded. A background noise signal of 0.25 mAU was determined using the 235 nm LED-based optical detection cell 100, which was comparable to the 0.30 mAU noise reported in the prior art solutions, such as by Silveira Petruci et al in "Absorbance detector for high performance liquid chromatography based on a deep-UV light-emitting diode at 235 nm", J. Chromatogr. A 1512 (2017) 143-146. By operating the UV-LED 140 at this low current, the issue of UV-LED 140 overheating was overcome and thus eliminated the need for a heat sink. Temperature measurements of the 235 nm LED 140 within the detector 100 over one hour of continuous operation is shown in FIG. 11. The temperature reading was recorded from the point of the LED 140 in which the highest temperature was observed.

Detector Stray Light and Effective Optical Path Length

Figure 12:
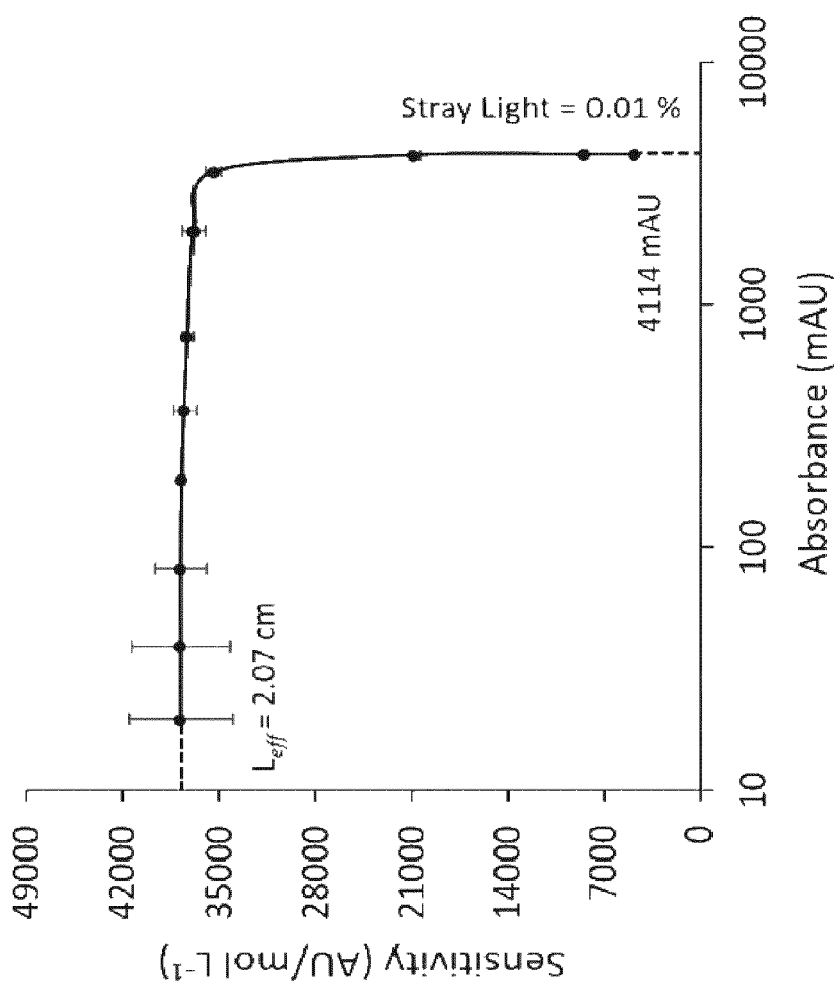
FIG. 12 shows a plot of detection sensitivity (AU/mol $L^{-1}$) versus absorbance.

The stray light and effective optical detection path 114 length associated with the fabricated UV optical cell was determined through the use of the azo dye Orange G. Effective pathlength, and stray light were determined using the same approach set out by Li et al. in "Performance of a new 235 nm UV LED-based on-capillary photometric detector", Anal. Chem. 88 (2016) 12116-12121. Effective pathlength ($L_{eff}$) and stray light were calculated using the plot of detection sensitivity (AU/mol $L^{-1}$) versus absorbance, as shown in FIG. 12. Extrapolation to the y-axis yielded a sensitivity value of 38000 AU/mol $L^{-1}$. Using this estimated value along with the molar absorptivity value of Orange G (18300 L mol-1 $cm^{-1}$), an effective pathlength of 2.07 cm was observed. This effective pathlength corresponded to 96.28% of the actual optical channel 114, also referred herein as optical detection path, length of the optical detection cell 100, which may be around 2.15 cm. The upper limit of the optical detection cell 100 linearity, corresponding to a 5% drop in sensitivity, was 3.162 AU. This observed upper linearity limit is higher than commercially available high sensitivity detection cells (detector linearity up to 2 AU), while at a fraction of the cost compared to the commercially available systems. The upper linearity limit value is also considerably higher compared to those recently reported for various capillary photometric detectors incorporating UV-LED light sources, ranging from 100-632 mAU. Following extrapolation to the x-axis, where sensitivity=0, an absorbance of 4.114 AU was observed which corresponds to a negligible stray light level of <0.01%. The stray light level observed most likely resulted as a consequence of the optical detection path 114 length, the UV-LED 140 being operated with a low intensity in combination with the UVC photodiode 160 and the fact the PMMA optical detection cell body 110 is non-transparent to UV light. This stray light is lower in comparison to other detection cells employing deep UV LEDs 140, such as the LED-based optical detection cell 100, also referred to simply as a detector, reported by Sharma et al. in "LED-Based UV Absorption Detector with Low Detection Limits for Capillary Liquid Chromatography", Anal. Chem. 87 (2015) 1381-1386, in which a stray light of 3.6% was observed. Similarly, the lowest stray light reported by Li et al. in "High sensitivity deep-UV LED-based z-cell photometric detector for capillary liquid chromatography", Anal. Chim. Acta 1032 (2018) 197-202. for high sensitivity, UV LED-based detector incorporating commercial z-cells was 3%.

Chromatographic Repeatability

The measurement repeatability associated with the UV-LED-based optical detector cell 100 combined with an Ion Chromatography (IC) set up was established through the analysis of a standard anion solution containing 0.5 mg L$^{-1}$ NO$_2^-$ and 2.5 mg L$^{-1}$ NO$_3^-$. The anion standard was injected thirty consecutive times. Retention time and peak area repeatability for both analytes are graphically presented in FIGS. 13a and 13b. Relative standard deviations (RSD) of retention times and peak areas for the 30 runs ranged from 0.75-1.10% and 3.06-4.19%, respectively. FIGS. 13a and 13b show the results of a repeatability study over 30 sequential runs, analysing 150 μL injection volume of a standard anion solution containing 0.5 mg L$^{-1}$ NO$_2^-$ and 2.5 mg L$^{-1}$ NO$_3$. The eluent used was 100 mM KOH at a flow rate of 0.8 mL min$^{-1}$ with AG15 guard column. (A) Repeatability of retention times for nitrite and nitrate overruns with associated RSD values. (B) Repeatability of peak area values determined for both analytes over 30 runs and associated RSD values.

Experimental system Analytical Performance and Sample Analysis

Under isocratic conditions using 100 mM KOH eluent, an AG15 column and a sample injection volume of 150 μL combined with the 235 nm optical detector with custom electronics both nitrite and nitrate are detected in under 2.5 minutes. A back pressure of 11.5 bar is generated by the system, which facilitates the potential of employing a portable pump with the detector. Linear ranges of 0.010-15 and 0.070-75 mg L$^{-1}$ were obtained for NO$_2^-$ and NO$_3^-$, respectively. A limit of detection (LOD) of 0.007 mg L$^{-1}$ for NO$_2^-$ and 0.040 mg L$^{-1}$ for NO$_3^-$ was observed. The LOD for each analyte was calculated, using a signal-to-noise ratio (S/N)=3.

A combination of blind standard solutions, environmental samples comprising one river water sample (Environmental A) and one water sample from a sugar processing plant (Environmental B), along with an Environmental Protection Agency (EPA) inter-calibration solution were analysed. The inter-calibration standard was provided by T.E. Laboratories and was a standard which is used within the Irish EPA Environmental Intercalibration Programme. This programme assesses analytical performance to ensure validity and comparability of environmental data for laboratories which submit data to the EPA. All samples were first filtered using 0.45 μm nylon filters to remove suspended particles. Nitrite and nitrate concentrations determined within each sample using the IC with 235 nm LED detector in comparison to concentrations determined using the accredited IC are shown in Table 1. The highest relative error observed for nitrite determination was −7.84% and for nitrate was 8.80%. The relative error obtained for the analysis of the EPA inter-calibration solution was 2.10%, highlighting acceptable accuracy demonstrated by the 235 nm LED optical detector and system.

TABLE 1

Concentrations determined using IC set-up and UV detector versus accredited IC (n = 3)

| Sample | Analyte | IC Set-up (mg L$^{-1}$) | Accredited IC (mg L$^{-1}$) | Relative Error (%) |
|---|---|---|---|---|
| A | Nitrite | 0.94 ± 0.015 | 1.02 ± 0.011 | −7.84 |
| B | Nitrate | 5.39 ± 0.040 | 5.07 ± 0.054 | 6.31 |
| Environmental | Nitrite | 0.51 ± 0.007 | 0.50 ± 0.005 | 2.00 |
| A | Nitrate | 5.07 ± 0.044 | 5.03 ± 0.037 | 0.79 |
| Environmental | Nitrite | 0.14 ± 0.008 | 0.15 ± 0.010 | −6.67 |
| B | Nitrate | 63.10 ± 0.323 | 58.00 ± 0.541 | 8.80 |
| EPA | Nitrate | 55.82 ± 0.925 | 54.67 ± 0.891 | 2.10 |

It is to be understood that the invention is not limited to the specific details described herein which are given by way of example only and that various modifications and alterations are possible without departing from the scope of the invention.

The invention claimed is:

1. An optical detection cell for the detection of inorganic analytes in a fluid sample, the optical detection cell comprising:
    a detection cell body comprising:
    a microfluidic channel having first and second ends, which is configured to provide an optical detection path for the fluid sample, a first opening for delivering a fluid sample to the microfluidic channel and a second opening for extracting fluid from the microfluidic channel, and
    first and second UV transparent windows attached respectively to opposing first and second locations of the microfluidic channel;
    an Ultra-Violet (UV) Light Emitting Diode, LED, proximally positioned to the first transparent window and configured when powered to emit a light at a UV wavelength range of 235.0 nm, which light is at least partially directed to the optical detection path of the microfluidic channel for the exposure of the fluid sample in the microfluid channel; and
    a light detector proximally positioned to the second transparent window and configured, when powered, for detecting the amount of UV light passing through the exposed fluid sample, the light detector being configured for generating at least one electrical signal having a value corresponding to the light being detected,
    wherein the UV-LED is configured to be driven by a constant electrical current having a value between 13.0 mA and 35.0 mA.

2. The optical detection cell of claim 1, wherein the diameter of the microfluidic channel is between 200.0 to 600 μm, preferably between 400.0 to 500.0 μm.

3. The optical detection cell of claim 1, wherein the optical detection path has a length between 1.0 cm to 2.5 cm, preferably between 2.0 cm to 2.5 cm, and even more preferably between 2.0 cm to 2.15 cm.

4. The optical detection cell of claim 1, wherein the UV-LED is configured to emit UV light at a range between 100.0 to 400.0 mm, preferably at a range between 200.0 to 300 mm, and more preferably at a range between 200.0 to 280.0 mm.

5. The optical detection cell of claim 1, wherein the transparent windows are UV transparent windows made from glass.

6. The optical detection cell of claim 1, wherein the light detector is a photodiode configured for detecting emitted light at the wavelength range of the UV-LED.

7. The optical detection cell of claim 1, wherein the microfluidic channel has a Z-shape or any other shape whereby the light source and the light detector can be positioned opposite one another.

8. The optical detection cell of claim 1, wherein the optical detection cell body comprises a first and a second layer bonded to one another.

9. The optical detection cell of claim 8, wherein a microfluidic channel is formed on the first layer and/or the second layer.

10. The optical detection cell of claim 9, wherein the first and second transparent windows are bonded on respective apertures created on the optical detection cell body.

11. The optical detection cell of claim 10, wherein the respective apertures are of equal size to the diameter of the microfluidic channel.

12. A method for using of the optical detection cell of claim 1 for detecting nitrite, nitrate, iodide, iodate and other inorganic analytes which absorb light within the UV wavelength of the light emitted from the UV-LED.

13. A portable system for detecting inorganic analytes in a fluid sample, the system comprising:
an optical detection cell comprising:
a detection cell body comprising:
a microfluidic channel having first and second ends, which is configured to provide an optical detection path for the fluid sample, a first opening for delivering a fluid sample to the microfluidic channel and a second opening for extracting fluid from the microfluidic channel, and first and second UV transparent windows attached respectively to opposing first and second locations of the microfluidic channel;
an Ultra-Violet (UV) Light Emitting Diode, LED, proximally positioned to the first transparent window and configured when powered to emit a light at a UV wavelength range of 235.0 nm, which light is at least partially directed to the optical detection path of the microfluidic channel for the exposure of the fluid sample in the microfluid channel; and
a light detector proximally positioned to the second transparent window and configured, when powered, for detecting the amount of UV light passing through the exposed fluid sample, the light detector being configured for generating at least one electrical signal having a value corresponding to the light being detected, wherein the UV-LED is configured to be driven by a constant electrical current having a value between 13.0 mA and 35.0 mA; and at least one pump module coupled to an opening of the optical detection cell body, the at least one pump module being configured for delivering a fluid sample to the optical detection path of the microfluidic channel for exposure to the UV-LED of the optical detection cell (100);
a sample intake module configured to provide a fluid sample of a predetermined volume to the at least one pump module;
a processing unit configured for processing the at least one signal generated by the light detector of the optical detection cell to compute the levels of inorganic analytes in the fluid sample; and
a power source providing at least one electrical signal for powering at least one of the optical detection cell, and/or the least one pump module, and/or the sample intake system, and/or the processing unit.

14. The system of claim 13, wherein the pump module comprises a pump configured for delivering eluent from an eluent source and a pump to inject sample to a micro-injection valve, the micro-injection valve configured with a predetermined sample loop enabling fluid sample and the eluent to be flushed into a guard column configured for separating anions in the fluid sample delivered to the optical detection cell.

15. The system of claim 14, wherein the sample intake system comprises at least one syringe for drawing a sample and injecting the sample into a microinjection valve.

16. The system of claim 13, wherein the processing unit is configured to control and operate one of the UV LED light source, the pumping module, and/or the sample intake system.

17. The system of claim 13, wherein the optical detection cell is secured on a base, the base comprising a UV-LED holder and a light detector holder.

18. The system of claim 17, wherein the base comprises means for guiding the UV-LED and light detector holders to the desired position with respect to the corresponding transparent windows.

19. The system of claim 18, wherein the guiding means are in the form of rails.

20. The system of claim 19, wherein the guiding means comprise means for securing the UV-LED and light detector holders at the desired position.

21. A method for using the system of claim 13 for detecting nitrite, nitrate, iodide, iodate and other inorganic analytes which absorb light within the UV wavelength of the light emitted from the UV-LED.

* * * * *